United States Patent
Lemaire

(10) Patent No.: US 7,405,241 B2
(45) Date of Patent: Jul. 29, 2008

(54) USE OF N₂O IN THE TREATMENT OF POST-ISCHEMIC BRAIN CELL DETERIORATION

(75) Inventor: Marc Lemaire, Paris (FR)

(73) Assignee: Air Liquide Sante (International), Paris (FR)

( * ) Notice: Subject to any disclaimer, the term of this patent is extended or adjusted under 35 U.S.C. 154(b) by 459 days.

(21) Appl. No.: 10/758,513

(22) Filed: Jan. 15, 2004

(65) Prior Publication Data

US 2004/0258766 A1 Dec. 23, 2004

(30) Foreign Application Priority Data

Jan. 15, 2003 (FR) .................................. 03 50002

(51) Int. Cl.
*A61K 47/00* (2006.01)
*A61M 15/00* (2006.01)
*A61M 16/00* (2006.01)
*A61M 37/00* (2006.01)
*A01N 25/00* (2006.01)

(52) U.S. Cl. ..................... 514/771; 128/203.12; 604/23
(58) Field of Classification Search ................. 514/769, 514/771, 959; 424/1.13; 604/23; 128/203.12, 128/204.18, 207.29
See application file for complete search history.

(56) References Cited

U.S. PATENT DOCUMENTS 3,876,773 A * 4/1975 Bracken ...................... 424/700
4,820,258 A * 4/1989 Mondain-Monval ........... 600/1

FOREIGN PATENT DOCUMENTS

| EP | 0 861 672 A | 9/1998 |
| FR | 2 812 545 A | 2/2002 |
| WO | WO 93/06869 | * 4/1993 |
| WO | WO 02 09731 A | 2/2002 |

OTHER PUBLICATIONS

Websters New World Dictionary Victoria Neufeldt ed. New York pp. 1067-1068.*
Homi et al. The Neuroprotective effect of Xenon Administration during Transient Middle Cerebral Artery Occlusion in Mice Anesthesiology 2003, 99, 876-881.*
Jevtovic-Todorovic et al. Nitrous oxide (laughing gas) is an NMDA antagonist, neuroprotectant and neurotoxin Nature Medicine 1998, 4 (4), 460-463.*
Kotwica et al. (Res. Exp. Med 1991, 191, 99-104).*
Tonner et al. (Best Practice Research Clinical Anaesthesiology 2001, 15(3) 491-503).*
French Search Report for FR 0350002.
Wang and Corbett, Brain Res., 533: 78, 1990.
Baldwin et al., Neurodegeneration 2: 139, 1993.
Chazot, Curr Opin Invest Drugs 1: 370, 2000.
Drian et al., Neurochem Int 38: 509, 2000.
Dirnagl et al., Trends Neurosci 22: 391, 1999.
Benes, Brain Res. Review 31: 251, 2000.
Burns et al., Psychopharmacology 115: 516, 1994.
Palmer and Widzowski, Amino acids 19: 151, 2000.
Franks et al., Nature 396: 324, 1998.
Jevtovic-Todorovic et al., Nature Med. 4: 460, 199.
Yamakura and Harris, Anesthesiology, 20008.

* cited by examiner

*Primary Examiner*—John Pak
*Assistant Examiner*—Ernst Arnold
(74) *Attorney, Agent, or Firm*—Christopher J. Cronin

(57) ABSTRACT

A medicinal composition and method to treat or minimize post-ischemic brain cell deterioration that comprises nitrous oxide or a nitrous oxide donor and xenon or a xenon donor. The medicinal composition may be administered prior to or subsequent to a stroke.

14 Claims, 3 Drawing Sheets

*P<0.05

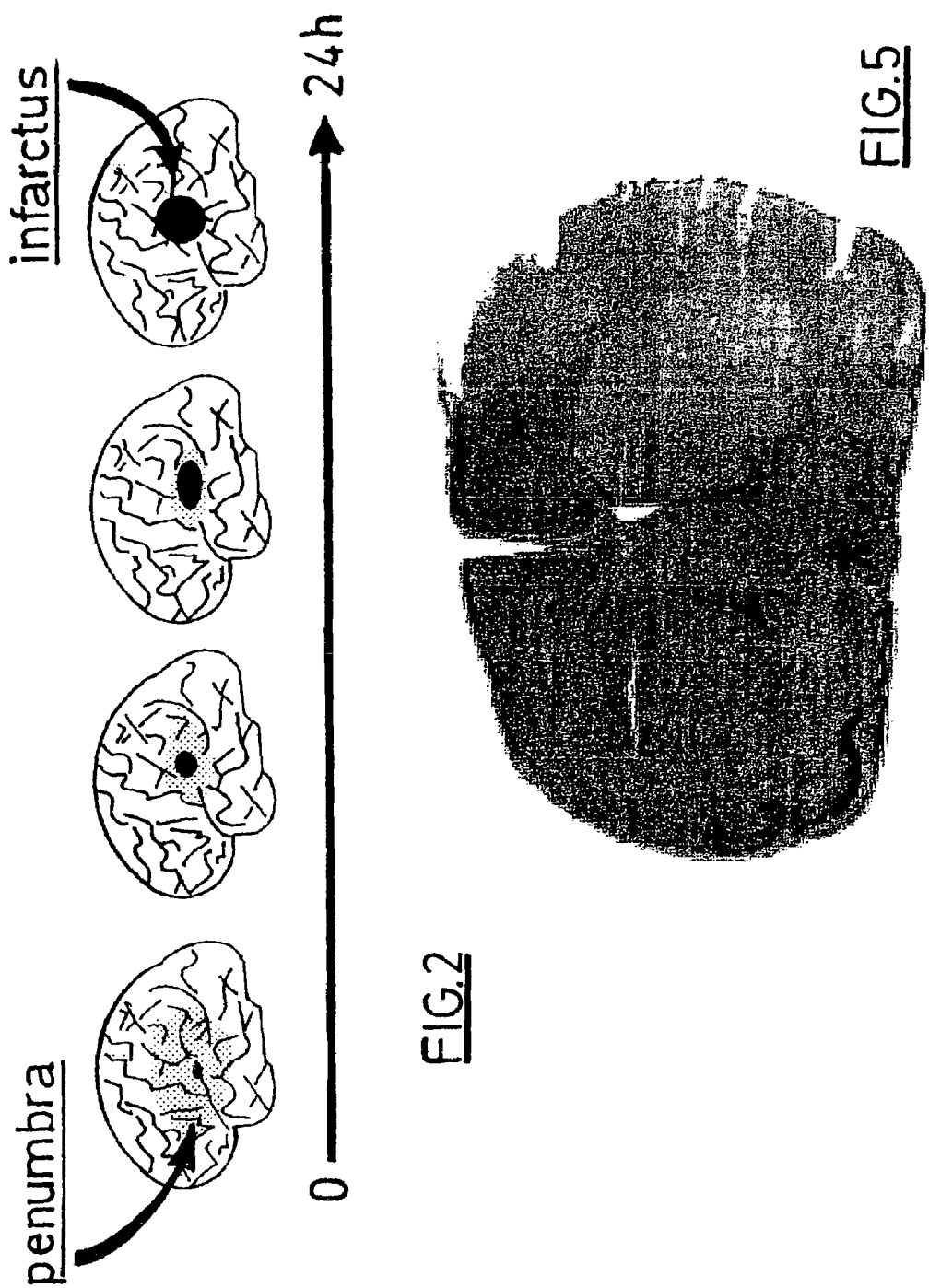

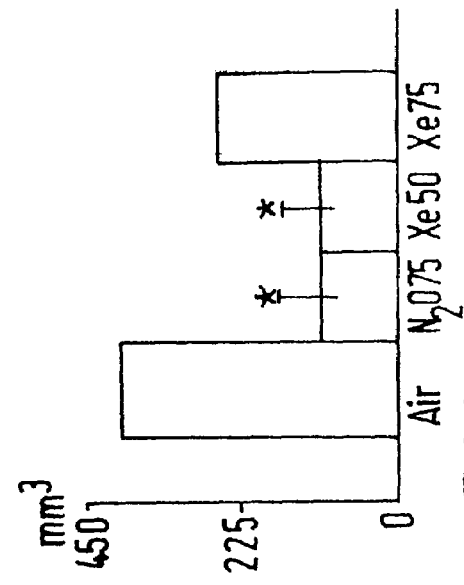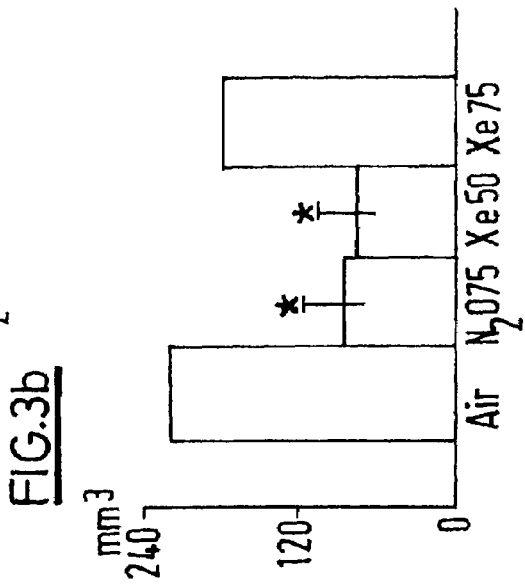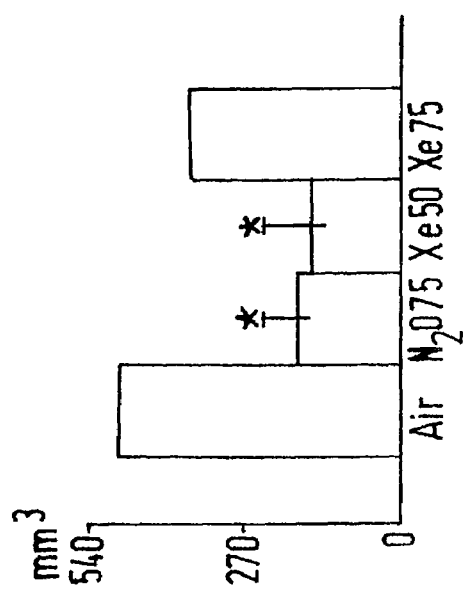

USE OF N₂O IN THE TREATMENT OF POST-ISCHEMIC BRAIN CELL DETERIORATION

BACKGROUND OF THE INVENTION

1. Field of the Invention

The invention relates to the use of nitrous oxide ($N_2O$) or of an $N_2O$ donor for producing all or part of a medicinal product intended to treat or prevent post-ischemic brain cell deterioration, in particular deterioration subsequent to a stroke, especially all or part of an inhalable gaseous medicinal product, in humans or animals.

2. Related Art

In cerebral ischemia subsequent to a stroke, and in strokes in general, a functional alteration of many neurotransmission systems is usually noted from a neurochemical point of view, in particular an increase in the release of glutamate, the excitotoxicity and contribution of which to neuronal death are known, as recalled by Dirnagl et al., *Trends Neurosci*, 22: 391, 1999.

Moreover, from a functional point of view, in the case of global ischemia in the rat, an increase is observed in locomotor activity, in particular described by Wang and Corbett, *Brain Res.*, 533: 78, 1990; Baldwin et al., *Neurodegeneration* 2: 139, 1993, the development of which is generally attributed to an alteration in cognitive functions of spatial recognition rather than to an alteration in sensory-motor functions.

As a result, a potential therapeutic role for ionotropic and metabotropic glutamergic receptor antagonists have been suspected, in particular by Chazot, *Curr Opin Invest Drugs* 1: 370, 2000; Drian et al., *Neurochem Int* 38: 509, 2001.

It also appears that the deleterious effects of known cerebral ischemias appear to involve localized ischemias which are thought to be caused by glutamergic excitotoxicity.

In fact, the therapeutic potential of glutamergic receptor antagonists is often put forward in the treatment of neuropathologies of excitotoxic origin, in particular cerebral ischemia, as described by Dirnagl et al., *Trends Neurosci* 22: 391, 1999, and productive disorders, as described by Benes, *Brain Res. Review* 31: 251, 2000.

However, the physiology of glutamergic receptors is complex and it appears that the high affinity antagonists may also exhibit neurotoxic properties, according to Burns et al., *Psychopharmacology* 115: 516, 1994.

Thus, a potential therapeutic advantage of low affinity antagonists, in particular for NMDA, has recently been proposed by Palmer and Widzowski, *Amino acids* 19: 151, 2000.

Moreover, document WO-A-02/09731 is also known, which relates to the use of CO, optionally supplemented with another gas, for treating inflammations of the upper respiratory tracts or of the bronchi. That document therefore targets the treatment of pathologies such as asthma, cystic fibrosis, pneumopathies or the like.

In addition, document EP-A-861672 teaches a method of treatment which can be used in emergency situations by administering various gases. However, this does not relate to post-ischemic brain cell degradations subsequent to strokes.

Finally, document FR-A-2812545 teaches a combination of gas and active product intended to treat or prevent pain. The active product is an analgesic, an anti-inflammatory, an antipyretic or the like.

SUMMARY OF THE INVENTION

To date, no effective medical product therefore exists for preventing or treating, at least partially, post-ischemic brain cell degradation subsequent to strokes.

The present invention falls within this context, and aims to provide all or part of a medicinal product which can be used for preventing, decreasing or treating any post-ischemic brain cell deterioration, in particular subsequent to a stroke, in humans or animals.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein:

FIG. 2 illustrates an engendered cerebral ischemia over a 24 hour period.

FIG. 3a illustrates that inhalation by the rats of nitrous oxide ($N_2O$) or of xenon (Xe) subsequent to ischemia makes it possible to considerably reduce the total volume of infarction, since a decrease in this volume of approximately 50% can be achieved in the case of inhalation of mixtures No. 2 and No. 3 instead of air (mixture No. 1 acting as control), and of approximately 30% when mixture No. 4 is inhaled.

FIGS. 3b to 3d confirm the results of FIG. 3a, since they make it possible to observe that inhalation of xenon or of $N_2O$ makes it possible to decrease, respectively, the post-ischemic volume of cortical infarction (FIG. 3b), the post-ischemic volume of striatal infarction (FIG. 3c) and the post-ischemic volume of oedema (FIG. 3d), compared to inhalation of air (control=mixture No. 1).

FIG. 5 illustrates a rat brain 24 hours after reperfusion, wherein thin sections 40 µm thick are cut and then stained with cresyl violet.

DESCRIPTION OF THE PREFERRED EMBODIMENTS

Figure 1:
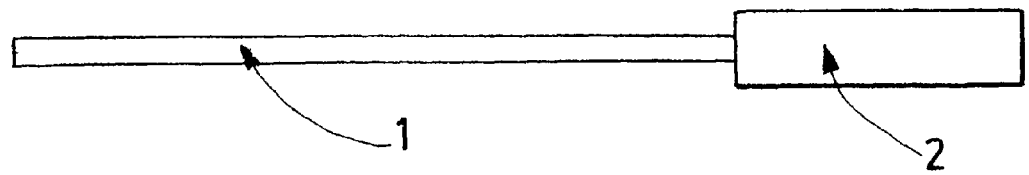
FIG. 1 illustrates a transient focal cerebral ischemia by middle cerebral artery occlusion (MCAO) with the introduction of a flexible nylon thread 1 (length 6.5 mm, diameter 180 µm), represented diagrammatically, a portion 2 of the proximal end of which has a diameter greater than that of the thread (length 3 mm, diameter 380 µm) into the vascular system of the rat.

The invention therefore relates to the use of nitrous oxide ($N_2O$) or of an $N_2O$ donor for producing all or part of a medicinal product intended to treat, minimize or prevent post-ischemic brain cell deterioration.

Depending on the case, the use of the invention may comprise one or more of the following technical characteristics:

all or part of the gaseous medicinal product is in inhalable form;

the post-ischemic brain deterioration results in or is subsequent to a stroke;

the nitrous oxide ($N_2O$) or the nitrous oxide donor is in gaseous form or is included in a gas or a mixture of gases;

the medicinal product contains an effective proportion of nitrous oxide ($N_2O$) or of $N_2O$ donor;

the medicinal product also contains xenon or a xenon donor, the xenon or the xenon donor being in gaseous form or being included in a gas or a mixture of gases;

the medicinal product contains an effective proportion of xenon or of a xenon donor;

the medicinal product also contains at least one other gaseous compound chosen from oxygen, nitrogen or argon, preferably nitrogen and oxygen;

the medicinal product contains an amount which is less than 60% by volume of xenon or of xenon donor, preferably less than or equal to 50% by volume;

the medicinal product contains an amount ranging up to approximately 80% by volume of $N_2O$ or of $N_2O$ donor, preferably up to 75% of $N_2O$;

the medicinal product contains from 19 to 25% by volume of oxygen and, optionally, of nitrogen.

The invention therefore also relates to an inhalable medicinal product with neuroprotective action in the brain, containing an effective amount of nitrous oxide ($N_2O$) or of a donor of such a compound, in particular intended to treat, minimize or prevent post-ischemic brain cell deterioration.

According to the case, the medicinal product of the invention may comprise one or more of the following technical characteristics:

it contains an amount ranging up to 80% by volume of gaseous $N_2O$;

it contains an effective amount of nitrous oxide ($N_2O$) or of a donor of such a compound;

it contains an effective amount of xenon or of a donor of such a compound;

it contains an amount which is less than 60% by volume of xenon;

it also contains from 19 to 25% by volume of oxygen and, optionally, of nitrogen.

The idea on which the present invention is based is to take advantage of the NMDA receptor antagonist properties of gaseous $N_2O$, optionally supplemented with xenon, for their neuroprotective nature, in prevention or treatment of post-ischemic pathologies subsequent to strokes.

EXAMPLES

In fact, recent studies, carried out in vitro, have shown that $N_2O$, and also xenon, can potentially behave like low-affinity antagonists of glutamergic receptors for N-methyl-D-aspartate, NMDA (Franks et al., *Nature* 396: 324, 1998; Jevtovic-Todorovic et al., *Nature Med.* 4: 460, 199; Yamakura and Harris, *Anesthesiology*, 20008).

Based on these observations, experiments were carried out in the context of the present invention, with the aim of determining the neuroprotective effects of $N_2O$ and of xenon, on neuronal death induced by transient cerebral ischemia in rats.

In order to demonstrate the beneficial effect of administering $N_2O$ or xenon on brain cells subsequent to cerebral ischemia, adult Sprague-Dawley rats weighing 350 g were subjected to the following experimental protocol.

On day 1, focal ischemia was induced in each of the rats by middle cerebral artery occlusion (MCAO), for a period of 1 h 30 minutes.

The transient focal cerebral ischemia by MCAO is obtained conventionally by introducing a flexible nylon thread 1, represented diagrammatically in FIG. 1 (length 6.5 mm, diameter 180 µm), a portion 2 of the proximal end of which has a diameter greater than that of the thread (length 3 mm, diameter 380 µm), into the vascular system of the rat, as far as the region of the ipsilateral hemisphere so as to cause an embolism therein, i.e. an ischemia.

Next, the rats are reperfused for 10 to 20 minutes, and are then made to inhale several mixtures of gases, namely:

mixture No. 1: air (control)

mixture No. 2: $N_2O$ (75% vol), the remainder being oxygen (25%)

mixture No. 3: xenon (50% vol), the remainder being oxygen (20 to 25%) and nitrogen (30 to 25%), respectively mixture No. 4: xenon (75% vol), the remainder being oxygen (25%).

On day 2, i.e. 24 hours after reperfusion, the rats are killed, the brains are recovered and frozen, and thin sections 40 µm thick are cut and then stained with cresyl violet, as shown in FIG. 5.

The volume of neuronal death is calculated, from the sections obtained after staining, in a conventional manner using an appropriate, commercially available conventional program.

In fact, as shown diagrammatically in FIG. 2, the cerebral ischemia engenders, in general, in 24 hours, an infarction in the region which has been subjected to ischemia (penumbra), leading to neuronal death in the brain cells present in a considerable portion of this region.

The results obtained during these measurements have been recorded in FIGS. 3a to 3d, which make it possible to visualize the post-cerebral ischemia neuroprotective effect of mixtures No. 2 to 4 above, in comparison with mixture No. 1 (air) which serves as a control.

Thus, FIG. 3a clearly shows that inhalation by the rats of nitrous oxide ($N_2O$) or of xenon (Xe) subsequent to an ischemia makes it possible to considerably reduce the total volume of infarction, since a decrease in this volume of approximately 50% can be achieved in the case of inhalation of mixtures No. 2 and No. 3 instead of air (mixture No. 1 acting as control), and of approximately 30% when mixture No. 4 is inhaled.

In this respect, it will also be noted that inhalation of 50% by volume of xenon (mixture No. 3) is more effective than inhalation of a higher dose of xenon, namely 75% (mixture No. 4), which implies that the most effective dose appears to be closer to 50% than to 75% with regard to xenon.

FIGS. 3b to 3d confirm the results of FIG. 3a, since they make it possible to observe that inhalation of xenon or of $N_2O$ makes it possible to decrease, respectively, the post-ischemic volume of cortical infarction (FIG. 3b), the post-ischemic volume of striatal infarction (FIG. 3c) and the post-ischemic volume of oedema (FIG. 3d), compared to inhalation of air (control=mixture No. 1).

Based on this observation, complementary examinations were carried out in order to determine the neurotoxic effects of the xenon and of the nitrous oxide ($N_2O$), at various amounts, compared to air, on brain receptors of the NMDA type.

Figure 4:
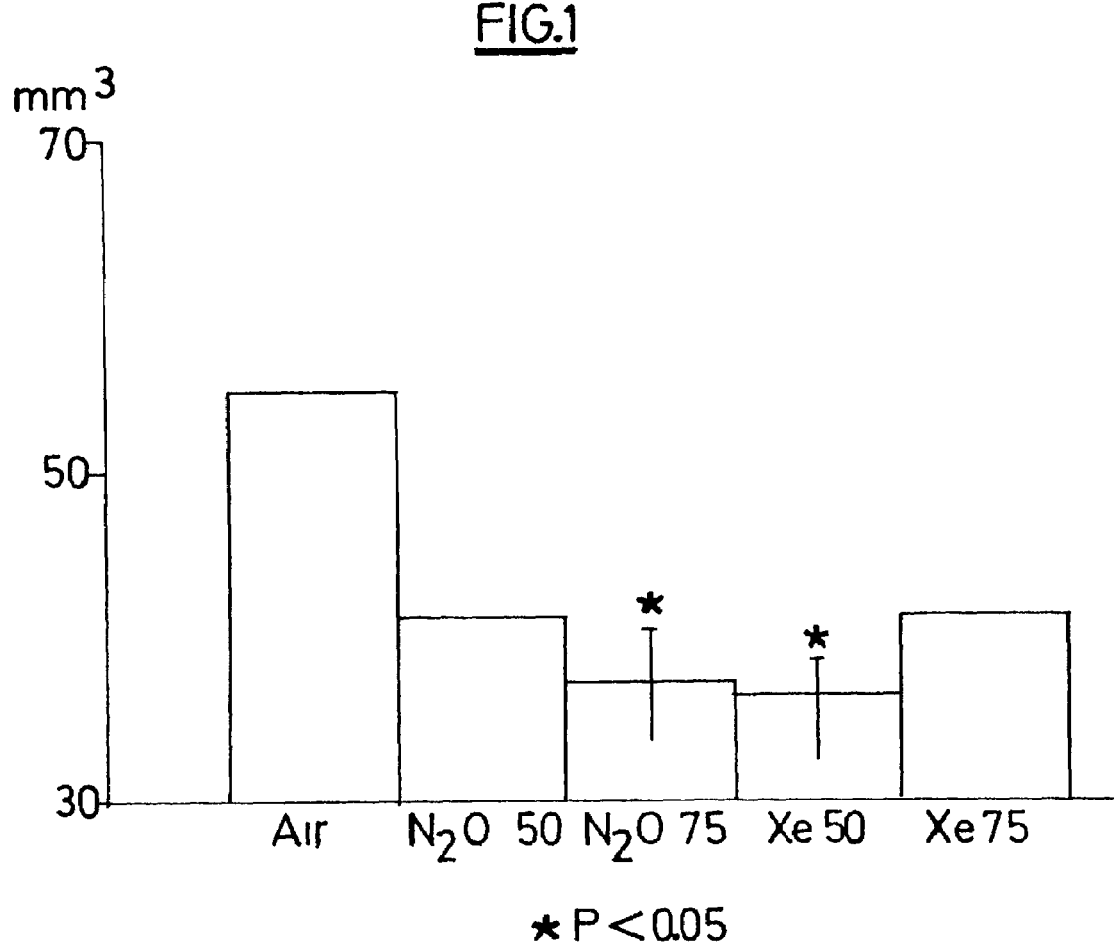
FIG. 4 illustrates that the administration of xenon or of nitrous oxide engenders a smaller volume (in $MN^3$) of deteriorated NMDA receptors than the control (air), this being with the nitrous oxide given at a dose of 50% or 75% by volume (remainder=25% of $O_2$) and the xenon given at a dose of 50% or 75% (remainder=mixture of 25% of $O_2$+25% of $N_2$, or, respectively, 25% of $O_2$).

The results of these examinations are reported in FIG. 4, which clearly shows that the administration of xenon or of nitrous oxide engenders a smaller volume (in $mn^3$) of deteriorated NMDA receptors than the control (air), this being with the nitrous oxide given at a dose of 50% or 75% by volume (remainder=25% of $O_2$) and the xenon given at a dose of 50% or 75% (remainder=mixture of 25% of $O_2$+25% of $N_2$, or, respectively, 25% of $O_2$).

However, a neurotoxic effect which is variable according to the dose administered thus emerges, leading to the observations that $N_2O$ at 75% and xenon at 50% by volume are more neuroprotective than $N_2O$ at a dose of 50% and xenon at a dose of 75%.

In other words, these data confirm that administration by inhalation of $N_2O$ at a dose of 75% by volume (or less) or of xenon at a dose of 50% by volume (or less) engenders a neuroprotective action with respect to cerebral ischemia and other similar excitotoxic diseases.

The inhalable medicinal product according to the invention is packaged in pressurized gas containers, such as gas bottles, and is dispensed to the patient via an appropriate system for administering gas, equipped with a breathing mask, a tracheal catheter, or the like.

Consequently, in the context of the invention, the use of gaseous nitrous oxide ($N_2O$) will be preferred to that of xenon, for producing a medicinal product intended to treat, minimize or prevent post-ischemic brain cell deteriorations, such as strokes.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A method for treating or minimizing, post-ischemic brain cell deterioration in humans comprising the step of administering by inhalation to a human a therapeutically-effective amount of a medicinal composition comprising 75 volume percent or less nitrous oxide and 50 volume percent or less xenon, at least part of said nitrous oxide and xenon being in gaseous form, thereby treating or minimizing post-ischemic brain cell deterioration in said human.

2. The method according to claim 1, wherein said method further comprises adding at least one component selected from the group consisting of oxygen, nitrogen, and argon to said medicinal composition.

3. The method according to claim 1, wherein said method comprises adding oxygen and nitrogen to said medicinal composition.

4. The method according to claim 1, wherein said nitrous oxide and xenon or are substantially in gaseous form.

5. The method according to claim 1, wherein said post-ischemic brain cell deterioration is subsequent to a stroke in said human.

6. The method according to claim 1, wherein said post-ischemic brain cell deterioration results in a stroke to said human.

7. The method according to claim 1, wherein said xenon and gaseous nitrous oxide are in gaseous form.

8. The method according to claim 1, wherein said medicinal composition further comprises from about 19% to about 25% by volume of oxygen.

9. The method according to claim 1, wherein said medicinal composition is placed in a pressurized gas container.

10. A method for treating or minimizing post-ischemic brain cell deterioration in humans comprising the step of administering by inhalation to a human a therapeutically-effective amount of a medicinal composition comprising a mixture of gaseous nitrous oxide and gaseous xenon, thereby treating or minimizing post-ischemic brain cell deterioration in said human, the nitrous oxide being present in an amount of 75 volume percent or less and the xenon being present at a concentration of 50 volume percent or less.

11. The method according to claim 10, wherein the medicinal composition further comprises oxygen.

12. The method according to claim 11, wherein said oxygen is present at a concentration of from about 19% to about 25% by volume of oxygen.

13. The method according to claim 10, wherein said post-ischemic brain cell deterioration is subsequent to a stroke in said human.

14. The method according to claim 10, wherein said post-ischemic brain cell deterioration results in a stroke in said human.

* * * * *